US007297668B2

(12) United States Patent
Johansson et al.

(10) Patent No.: US 7,297,668 B2
(45) Date of Patent: Nov. 20, 2007

(54) COMPOSITION

(75) Inventors: Marie Johansson, Watchung, NJ (US); John Ghaim, Franklin Park, NJ (US); Nadia Soliman, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 188 days.

(21) Appl. No.: 10/406,123

(22) Filed: Apr. 3, 2003

(65) Prior Publication Data

US 2004/0198620 A1    Oct. 7, 2004

(51) Int. Cl.
*C11D 3/382* (2006.01)
*C11D 3/44* (2006.01)
*C11D 3/20* (2006.01)

(52) U.S. Cl. ............... 510/157; 510/130; 510/132; 510/137; 510/139; 510/153; 510/205; 510/395; 510/407; 510/432; 510/437

(58) Field of Classification Search .......... 510/130, 510/132, 137, 139, 153, 157, 205, 395, 407, 510/432, 437
See application file for complete search history.

(56) References Cited

U.S. PATENT DOCUMENTS

| | | | |
|---|---|---|---|
| 2,438,091 A | | 3/1948 | Lynch |
| 3,277,013 A | | 10/1966 | Gianladis |
| 3,645,904 A | | 2/1972 | Beach |
| 4,035,514 A | | 7/1977 | Davis |
| 4,155,870 A | | 5/1979 | Jorgensen |
| 4,673,526 A | * | 6/1987 | Zabotto et al. ............. 510/139 |
| 4,784,788 A | | 11/1988 | Lancz |
| 5,246,613 A | | 9/1993 | Gilbert et al. |
| 5,266,321 A | | 11/1993 | Shukuzaki et al. |
| 5,431,913 A | * | 7/1995 | Phillips ....................... 424/401 |
| 5,527,488 A | * | 6/1996 | Groh ........................... 510/136 |
| 5,679,326 A | * | 10/1997 | Bara et al. ................... 424/70.1 |
| 5,830,445 A | * | 11/1998 | Bouillon et al. .............. 424/69 |
| 5,888,951 A | * | 3/1999 | Gagnebien et al. ......... 510/130 |
| 5,891,449 A | * | 4/1999 | Daniel et al. ................ 424/401 |
| 6,013,270 A | | 1/2000 | Hargraves et al. |
| 6,103,644 A | | 8/2000 | Sheridan |
| 6,120,759 A | * | 9/2000 | Bouillon ................... 424/78.31 |
| 6,217,889 B1 | | 4/2001 | Lorenzi et al. |
| 6,290,976 B1 | * | 9/2001 | Messenger ................... 424/401 |
| 6,524,594 B1 | * | 2/2003 | Santora et al. .............. 424/401 |
| 2003/0133900 A1 | * | 7/2003 | McLaughlin ............. 424/70.22 |
| 2003/0211062 A1 | * | 11/2003 | Laden et al. ................ 424/70.1 |
| 2005/0002973 A1 | | 1/2005 | Johansson et al. |
| 2005/0158351 A1 | | 7/2005 | Soliman et al. |

FOREIGN PATENT DOCUMENTS

| | | |
|---|---|---|
| CN | 1088776 | 7/1994 |
| WO | 01/85103 | * 11/2001 |
| WO | WO 0185103 | 11/2001 |

OTHER PUBLICATIONS

Flick, Ernest W. "*Cosmetics Additives: An Industrial Guide*". Noyes Publications. 1991.
Prosecution History from U.S. Appl. No. 10/612,549.
File History from U.S. Appl. No. 11/010,573, filed Dec. 14, 2004.
Supplemental File History from U.S. Appl. No. 10/612,549, dated Jul. 2, 2003.

* cited by examiner

*Primary Examiner*—Charles Boyer
(74) *Attorney, Agent, or Firm*—Michael F. Morgan

(57) ABSTRACT

A skin composition which is at least substantially anhydrous and comprises
  a) At least one water immiscible emollient oil in sufficient quantity to provide emolliency to skin,
  b) At least one emulsifying agent capable of forming an emulsion, in situ, on the skin with the above oil when water is added to the said composition, the said emulsifier in such quantities that the oil is substantially removed from the skin,
  c) A water soluble, at least substantially insoluble in the composition skin exfoliative and/or skin polishing material in sufficient quantities to remove dead cells from the skin during application of the composition and,
  d) At least one wax in sufficient quantity to at least enhance the physical stabilization of the composition.

3 Claims, No Drawings

COMPOSITION

BACKGROUND OF THE INVENTION

Aqueous skin cleansing compositions have been used for centuries. The problems with them are well known with respect to removing oil based skin deposits or leaving the skin too dry. Likewise oil-in-water and water-in-oil emulsions also have various difficulties. These and various other issues have been disclosed in WO 01/85103, published on Nov. 15, 2001.

Prior attempts have been made to overcome the foregoing problems of aqueous emulsions by employing anhydrous skin cleansers. Anhydrous skin cleansers, sometimes called waterless cleansers, typically contain high concentrations of water-insoluble solvents, which makes them generally effective at removing oily undesirable moieties from the skin, but less effective in removing water-soluble undesirables. Further, anhydrous skin cleansers typically are not cosmetically elegant tending to have a heavy, greasy feel making them unappealing to the touch and are not easily removed from the skin. They generally must be wiped off with toweling, leaving the skin feeling greasy or need to be washed off with strong soap, leaving the skin feeling harsh and dry.

Various solutions to these problems have been proposed in the prior art. For example, U.S. Pat. No. 4,673,526 proposes an anhydrous three component system designed for skin cleansing having a solid particulate matter of various polymers to remove oily particles while being essentially multiphase. The publication WO 01/85103 discloses a substantially anhydrous four component system comprising a) at least one water-immiscible cosmetic emollient oil, the cosmetic emollient oil comprising a major portion of the formulation; b) at least one oil-gelling agent that is both water-insoluble and oil-insoluble; c) at least one emulsifying agent capable of forming an emulsion, in situ, on the skin when a small amount of water is added gradually to the substantially anhydrous formulation during use; and d) a substantially crystalline water-soluble, abrasive material that is substantially insoluble in the substantially anhydrous vehicle of the formulation.

However, each one of them is not totally satisfactory in at least one parameter. A composition within WO 01/85103 has 5-8 wt % oil separation at the top, for example. Because of separation, obtaining the same product distribution with continuous uses and, therefore, giving equivalent benefits is difficult. Additionally, the U.S. Pat. No. 4,673,526 patent composition is limited to cleansing by removal of oily substances on the skin without the addition of fat bodies to the skin. The WO 01/85103 composition should be removed from the skin with a relatively small amount of water, preferably up to 2 parts of the actual oily composition on the skin. These, and other disadvantages can be overcome by the discovery and use of a new at least substantially anhydrous skin cleansing composition.

The present anhydrous skin cleansers provide skin cleansing exfoliation and/or polishing in a cosmetically aesthetic vehicle while, at the same time, leaving the skin exceptionally soft, smooth and moisturized. The composition has at least enhanced phase stability, can polish and/or exfoliate the skin, and can be effectively removed from the skin with varying amounts of water.

SUMMARY OF THE INVENTION

In accordance with the invention, there is a composition which is at least substantially anhydrous and comprises:

a) at least one water insoluble emollient oil in sufficient quantity to provide emolliency to the skin,
b) at lease one emulsifying agent capable of forming an emulsion in situ on the skin with the above oil when water is added to the said composition,
c) exfoliative and/or polishing material in sufficient quantities to remove cell debris from the skin during application of the composition.
d) at least one wax in sufficient quantity to at least enhance the physical stabilization of the composition.

A further aspect of the invention is the application of this composition to the skin, working the composition into the skin, adding water to the composition on the skin, with continual working into the skin, if desired, and then removing from the skin as a solution or an aqueous emulsion.

DETAILED DESCRIPTION OF THE INVENTION

At least one water immiscible emollient oil component is present in the composition. Illustrative examples of the oil(s) include:

1. Mineral oils: paraffin oil, petroleum jelly oil.
2. Animal oils: Purcellin oil, perhydrosqualene, fish oils and lanolin oil.
3. Vegetable oils: Sweet almond oil, palm oil, calophyllum oil, avocado oil, olive oil, castor oil, cereal germ oil such as oil of wheat germs, canola oil, sunflower oil, soybean oil and jojoba oil.
4. Silicone oils: Dimethylpolysiloxane, cyclomethicone
5. Esters: Butyl myristate, isopropyl myristate, cetyl myristate, isopropyl palmitate, butylstearate, hexadecyl, stearate, isopropyl stearate, octyl stearate, isoceryl stearate, decyl oleate, hexyl laurate di-caprylate of proplyene glycol, di-isopropyl adipate
6. The organic alcohols: Oleic alcohol, linoleic alcohol, linolenic alcohol, isostearyl alcohol, octyl dodecanol
7. The esters derived from lanolic acid: Isopropyl lanolate, isocetyl lanolate
8. Free fatty acid including linoeleic, myristic, palmitic, stearic and the like.

In addition to the classes of the compounds mentioned above, one can also utilize as additional illustrative oils the acetyl glycerides, the octanoates and decanoates of alcohols and polyalcohols such as those of glycol and glycerol, the ricinoleates of alcohols and polyalcohols such as that of cetyl.

The oil or oils can be in the composition at a minimum of about 15, 20, 25, or 30 wt % of the composition. The maximum amount of oil can be up to about 85, 75, 65, or about 60 wt % of the composition.

The emulsifier, component b, is also an important portion of the composition. The ability to emulsify the oil, component a, when water is added, is a significant effect of the composition. This provides a clean surface to the skin after water is added but still allows the skin to benefit from the emolliency of the oil. To facilitate the forming of an emulsion upon the first addition of water to the composition in contact with the skin more than one emulsifier can be employed. Therefore, it is preferred to use a mixture of at least two emulsifiers, one having a relatively low HLB value preferably of not more than 8, more preferably in the range of about 3 to about 7, and one having a relatively high HLB of preferably at least 8, more preferably in the range of about 10 to about 19. "HLB" refers to the well known calculated Hydrophile-Lipophile-Balance value assigned to emulsifiers, most commonly nonionic emulsifiers, relating to the water solubility of the emulsifier. An explanation of the HLB system is given in "The HLB System, A Time Saving Guide to Emulsifier Selection" by ICI Americas, Inc., Wilmington Del., 19897, 1984.

The anhydrous skin composition of the present invention readily form an emulsion when the anhydrous skin composition is contacted with water. Thus, this invention beneficially retains the cell debris removal efficacy without an unwanted oily residue but leaving the skin feeling smooth and moisturized.

Exemplary emulsifying agents include, without being limited thereto, ethoxylated carboxylic acids, exthoxylated glycerides, glycol esters and derivatives thereof, monoglycerides, polyglyceryl esters, polyhydric alcohol esters and ethers, sorbitan/sorbitol esters, triesters of phosphoric acid, ethoxylated-fatty alcohols, propoxylated polyoxyethylene (POE) ethers and the like and mixtures thereof. Particularly preferred are glyceryl stearate, PEG-100 stearate, sorbitan stearate, PEG-40 stearate, steareth-2, steareth-20, steareth-100, polysorbate-20, laureth-12, laureth-23, polysorbate 80, sucrose distearate, glyceryl oleate, and the like as well as mixtures thereof.

Generally, at least about 1 wt % of the composition is emulsifier(s), or at least about 2 wt %. Usually no more than about 15 wt % of an emulsifier(s), based upon weight of the composition, is necessary, though no more than about 10 wt % can also be employed.

Component c provides the polishing and/or exfoliative action to the skin. Illustrative exemplification of these materials are salts, polymers and the like. Examples of salts include Dead Sea salt, salts of Group IA and IIA metals and ammonia including for example, sodium chloride, potassium chloride, sodium nitrate, magnesium sulfate, ammonium chloride and the like. Additionally materials such as sugars, starch, urea and water-soluble urea derivatives such as allantoin can also be used. Some of these materials are substantially crystalline. One or more of these water-soluble materials are employed, preferably having sufficient water solubility such that at least about 15 parts by weight of the material will dissolve in 100 parts by weight of water at 20° C., also including at least about 25 or 30 parts solubility and which are insoluble in the anhydrous skin cleanser composition. The particle size of the material should be sufficiently large to serve as a scrubbing and/or polishing agent against the skin to remove dirt and cellular debris, such as rough dead skin cells, and yet not so large as to scratch or irritate the skin.

Although salts, urea, starch and the like can be polishers of skin as well, it is generally preferred to use the polymers as polishing agents although they can have exfoliative characteristics as well. Examples of polymers include:
1. The xanthan gums, which are heteropolysaccharides, notably the products known under the commercial names of KELTROL and KELTROL F by the CP KELCO Company, as well as the product known under the commercial name of RHODOPOL 23 and RHODI-ACARE T sold by RHODIA, INC.
2. The carboxymethy starch, notably the product sold under the commercial name of PERFECTAMYL GEL 45 and PERFECTAMYL GEL MB by the AVEBE Company.
3. The cellulose ethers such as ethylhydroxyethylcellulose, sold under the commercial name of "BERMOCOLL" by the AKZO NOBEL Company.
4. The hydroxyalkylcelluloses such as hydroxyethylcellulose and hydroxypropylmethylcellulose, sold under the commercial name of CELLOSIZE by AMERCHOL CORPORATION, or under the commercial name of NATROSOL by the HERCULES, INC. or under the commercial name of METHOCEL by the DOW CHEMICAL Company, including METHOCEL E50. The hydroxypropyl starch notably the products sold under the commercial names of ZEINA B860 by the GRAIN PROCESSING CORPORATION.

These polymers desirably have an approximate granulometry allowing a gentle and non-irritating action.

Component c materials, particularly the salts, are generally employed at a minimum level sufficient to provide a skin exfoliative, cleansing, skin debris removal effect. Generally, at least about 1, 2, 3, or 5 wt % of the composition is employed desirably at least about 10 or 15 wt %. No more than about 50 wt % of salts is necessary with quantities not exceeding about 40, 30 or 25 wt % being also beneficial.

The polymers of component c, such as enumerated above, plus starch, sugar and the like can be employed at quantities at least about 1, 2, 3 or 5 wt % of the composition, desirably at least about 2 wt %. Generally, no more than about 50 wt % of the composition can be employed with quantities not exceeding about 40, 30, 25 or 20 wt % being also beneficial. Mixtures of the various components, for example, mixtures of polymers and mixtures of salt (ionics) and polymers can be used.

Component d is the wax material. These materials provide the enhanced phase integrity to the overall composition. When this component is absent, the composition disperses into separate phases, the latter oil phase rising to the top with the heavier salt/polymer materials sinking to the bottom. This provides an unpleasing appearance to the composition, particularly when it is in a container wherein the composition is "scooped" therefrom as well as presenting a serious potential issue of using a composition richer in one component and/or poorer in one component each time the composition is employed. When a wax is used a single, at least essentially visually homogeneous phase for the composition can be obtained. The previously enumerated disadvantages are avoided or essentially reduced. With a physically stable phase present, the delivery (storage) vehicle possibilities are expanded substantially. For example, the composition can be loaded into a container such as a tube capable of deformation wherein a uniform or at least substantially uniform composition can be delivered to the skin upon pressure deformation of the container's exterior.

Illustrative examples of waxes include:
1. The mineral waxes: microcrystalline waxes, paraffin, petroleum jelly,
2. The fossil waxes: ozokerite, montan wax,
3. Animal waxes: beeswax, spermaceti, lanolin wax, lanolin derivatives such as lanolin alcohols, hydrogenated lanolin, hydroxylated lanolin, acetylated lanolin, fatty acids of lanolin, acetylated lanolin alcohol,
4. Vegetable waxes: candelila wax, carnauba wax, sumac wax, cocoa butter wax, and shea butter,
5. Hydrogenated waxes which are solid at 25° C.; hydrogenated castor oil, hydrogenated palm oil, hydrogenated tallow, hydrogenated cocoa oil, hydrogenated soy oil,
6. Synthetic oils: polyethylene, copolymerized polyethylene waxes,
7. The fatty esters which are solid at 25° C.: monomyristate of propylene glycol, myristyl myristate,
8. Silicone oils: methyloctadecane-oxypolysiloxane and poly (dimethylsiloxy) stearoxysiloxane, dimethicone, cyclomethicone.

Among the waxes, the following compounds can also be utilized: Cetyl alcohol, stearyl alcohol, the mono-, di- and tri glycerides which are solid at 250° C., stearic monoethenolamide, colophane and its derivatives such as abietates of glycol and glycerol, the sucroglycerides. In general, a wax is a long chain hydrocarboanaecous material which is at least substantially solid at 25° C., and is preferably solid.

The quantity of wax employed in the composition is that amount which enhances phase stabilization. Generally at least about 1, 1.5, or 2 wt % of the composition can be employed, desirably at least about 2 or 3 wt %. Usually no more than about 10 or 15 wt % of the composition is wax. Mixtures of waxes can be employed.

With respect to various terms employed in the specification and claims "substantially anhydrous" means less than about 5 wt % water in the composition, preferably less than about 3 wt % water, more preferably less than about 1.5 wt % water and most preferably 0 to about 1 wt % water. In measuring the water amount, any water of crystallization of a salt is not counted in "substantially anhydrous".

The viscosity of the composition is generally that of a thick liquid or gel but can reach a pasty, paste like consistency. Generally, the viscosity is a minimum of about 10,000 or 15,000 preferably 20,000 to a maximum of about 12,000,000, 2,000,000 or even 600,000 cps.

Viscosity is measured by standard techniques such as the use of a Brookfield Viscometer. Those skilled in the art will use the appropriate spindle and speed combination to cover the range of viscosity to be measured. For less viscous samples, Brookfield spindle #5, at 20 rpm and 20° C. is suitable. At high viscosities, a helipath attachment is used with for example, spindle T-E at 2.5 rpm and 20° C. For example, a preferred range of viscosity of about 500,000 to 1,200,000 cps is measured with a Brookfield viscometer using a helipath attachment with a T-E spindle at 2.5 rpm and about 20° C.

The anhydrous skin compositions of this invention can be prepared by heating together the emollient water-immiscible oil ingredients and emulsifier ingredients to a temperature of about 70° C. with sufficient mixing agitation to dissolve the emulsifier in the oil to provide a substantially anhydrous oil-emulsifier phase. The wax is then dispersed with mixing agitation in the anhydrous oil-emulsifier phase until a substantially non-runny, thickened phase begins to form, cooling the admixture, if necessary. The water-soluble exfoliative/polishing ingredient, for example, salt, sugar and/or polymer and optional ingredients, if any, are then added to the composition with sufficient mixing agitation to evenly disperse the ingredients into the composition. Those skilled in the art will understand that the order of incorporation of ingredients and temperatures employed may vary with the type of ingredient and the manner of dissolution recommended by the supplier of the material.

A preferred embodiment for using substantially anhydrous skin compositions formulated according to the invention comprises the following steps:

a) Applying the anhydrous skin cleanser to substantially dry (not wet) skin, preferably by manually rubbing the applied amount over the skin to thoroughly coat the skin. The rubbing action preferably is a gentle rubbing or massaging for a period of at least about 5 seconds, preferably about 5 to about 30 seconds, to promote the removal of oily or greasy, water-insoluble soils and skin cell residues.

b) Contacting the skin cleanser coated skin with an amount of water sufficient to moisten the coated skin, further continuously rubbing and massaging the so-moistened skin until the abrasive ingredient particles substantially dissolve. The formation of an emulsion in situ on the skin can be observed as a change in the appearance of the substantially transparent or translucent coating to a substantially turbid (i.e., milky to opaque) liquid emulsion.

c) Removing the resultant emulsion from the skin, preferably by rinsing it off with additional water. The intermediate step b need not be followed. Effective skin emolliency and removal of the composition can both be accomplished by adding water of small, medium or large quantities. The skin can then be dried.

Step "b" is preferably performed by wetting the skin with tap water and massaging while rinsing the coated skin. Alternatively, a measured amount of water can be applied, if desired. Dissolution of the abrasive ingredients can be determined during step "b" by a change in the tactile characteristic of the skin cleanser on the skin from generally grainy to generally smooth.

It is recognized that in step "c" the emulsion can also be wiped off first and the wiped skin be then rinsed. Preferably, the novel skin compositions are readily and conveniently removable from the skin by rinsing with water, thereby eliminating the need for tissues or towels and avoiding disposal or laundry problems attendant with the use thereof.

Anhydrous skin formulations prepared with the component and ranges disclosed possess a surprising combination of beneficial effects when used on soiled skin. The term "soil" as applied to skin includes soils from natural sources, such as cellular debris present on the skin, and soils from external sources topically applied to the skin, such as from makeup, cosmetics, etc. industrial greases, and environmental dirt. The anhydrous skin compositions can thoroughly cleanse the skin of makeups and other water-immiscible cosmetic residues. They effectively remove various types of oily and greasy soils from the skin surface and difficult to solubilize residues. The anhydrous skin compositions can remove rough and dry skin cells. Moreover, the anhydrous skin compositions can smooth and polish the skin surface and leave the skin soft and moisturized.

The following examples further illustrate the anhydrous skin compositions of this invention with specific embodiments, ingredients and methods but are not intended to be limiting.

Below is a preferred example, together with various preferences; all numbers are approximate:

EXAMPLE 1

20-90% oil, for example a vegetable oil like canola oil, preferably 30-80, more preferably 50-80

5-25% Stearic acid, preferably 7-20% more preferably 8-15

0.25-5% of glycerol stearate preferably 0.5-4% more preferably 0.75-3%

0.25-5% PEG-100 stearate preferably 0.5-4% more preferably 0.75-3%

0.05-5% sucrose distearate preferably 0.1-3% more preferably 0.2-2%

0-5% of shea butter preferably 0.1-4% more preferably 0.2-3%

0.1-5% cetyl alcohol preferably 0.3-3% more preferably 0.5-2%

0.5-5% stearyl alcohol preferably 0.3-3% more preferably 0.5-2%

0.5-5% beeswax preferably 0.75-4% more preferably 1-3%

0-10% maltodextrin preferably 0.5-5% more preferably 1-4%

0-10% colloidal oatmeal preferably 0.5-8% more preferably 1-5%
5-50% sodium chloride or sugar preferably 8-45% more preferably 10-40%
0-5% silicone oil

EXAMPLE 2

| Components | Wt % |
|---|---|
| Canola oil | 49.30 |
| Stearic acid | 10.00 |
| PEG-100-Stearate | 1.5 |
| Glycerol Stearate | 1.5 |
| Sucrose Distearate | 0.5 |
| Shea butter | 0.50 |
| Cetyl alcohol | 1.6 |
| Stearyl alcohol | 0.6 |
| White beeswax | 2.00 |
| Maltodextrin | 2.00 |
| Collodial oatmeal | 2.00 |
| Sodium chloride | 27.80 |
| Fragrance | 0.40 |
| Preservative | 0.30 |
| Totals | 100.00 |

The components were mixed together.

Samples were placed in 4 oz glass containers and allowed to age at various temperatures. Appearance of phase separation was examined by visual inspection. Amount of separation was estimated by dividing the volume of separated liquid by the total volume in the sample container.

No visual phase separation occurred at 77° F. and 110° F. for 49 days.

EXAMPLE 3

| Components | Wt % |
|---|---|
| Canola oil | 47.40 |
| Carnauba wax | 2.00 |
| Stearic acid | 10.00 |
| PEG-100-Stearate | 1.5 |
| Glycerol Stearate | 1.5 |
| Shea butter | 0.50 |
| Cetyl alcohol | 1.6 |
| Stearyl alcohol | 1.6 |
| White beeswax | 2.00 |
| Sucrose Distearate | 0.50 |
| Maltodextrin | 2.00 |
| Collodial oatmeal | 2.00 |
| Sodium Chloride | 26.95 |
| Polysorbate80 | 0.75 |
| Fragrance | 0.40 |
| Preservative | 0.30 |
| Totals | 100.00 |

Following the protocol of Example 2, there was no visual phase separation at 77° F. and 110° F. for 104 days.

Comparative Example—An anhydrous exfoliation scrub having the label components below which meet the WO 01/85103 component description was purchased at the retail store Crabtree and Evelyn and tested according to the protocol of Example 2. A 5% phase separation occurred at 110° F. after 22 days and a 9% phase separation occurred at 77° F. after 22 days following the protocol of Example 2.

Component list for comparative example:

Macadamia ternifolia seed oil, sodium chloride, calcium stearate, maltodextrin, emulsifying wax NF, isopropyl myristate, butyrospermum park 11, (shea butter), colloidal oatmeal USP, sodium methyl cocoyl taurate, fragrance (parfum), lavandula angustifolia (lavender) oil, stearic acid, caprylic/capric triglyceride, cyclomethicone, sucrose distearate, cetyl alcohol, cetearyl alcohol, behentrimonium methosulfate, potassium stearate, phenoxyethanol, methylparaben, ethylparaben, propylparaben, butylparaben, isobutylpraben.

The invention claimed is:

1. A composition comprising
   a) 30 to about 90 weight % vegetable oil.
   b) about 5 to about 25 weight % stearic acid.
   c) about 0.25 to about 5 weight % glycerol stearate,
   d) about 0.25 to about 5 weight % PEG-100 stearate,
   e) about 0.05 to about 5 weight % sucrose distearate.
   f) 0 to about 5 weight % shea butter.
   g) about 0.1 to about 5 weight % cetyl alcohol.
   h) about 0.5 to about 5 weight % stearyl alcohol.
   i) about 0.5 to about 5 weight % beeswax.
   j) 0 to about 10 weight % maltodextrin.
   k) 0 to about 10 weight % colloidal oatmeal.
   l) about 5 to about 50 weight % sodium chloride, sugar, or both sodium chloride and sugar.
   m) 0 to about 5 weight % silicone oil.

2. A composition comprising about 49.3 weight % canola oil. about 10 weight % stearic acid. about 1.5 weight percent glycerol stearate, about 0.5 weight % sucrose distearate, about 0.5 weight % shea butter, about 1 .6 weight % cetyl alcohol, about 0.6 weight % stearyl alcohol, about 2 weight % white beeswax, about 2 weight % maltodextrin. about 2 weight % colloidal oatmeal. and about 27.8 weight % sodium chloride.

3. A composition comprising about 47.4 weight % canola oil. about 2 weight % carnauba wax, about 10 weight % stearic acid, about 1.5 weight % PEG-100 stearate. about 1.5 weight % glycerol stearate, about 0.5 weight % shea butter. about 1.6 weight % cetyl alcohol. about 1.6 weight % stearyl alcohol. about 2 weight % white beeswax. about 0.5 weight % sucrose distearate, about2 weight % maltodextrin, about 2 weight % colloidal oatmeal, about 26.95 weight % sodium chloride, and about 0.75 weight %.polysorbate 80.

* * * * *